(12) United States Patent  (10) Patent No.: US 7,632,791 B2
Kraft  (45) Date of Patent: Dec. 15, 2009

(54) SPIROCYCLIC KETOLS AND THEIR USE

(75) Inventor: Philip Kraft, Dübendorf (CH)

(73) Assignee: Givaudan SA, Vernier (CH)

( * ) Notice: Subject to any disclaimer, the term of this patent is extended or adjusted under 35 U.S.C. 154(b) by 252 days.

(21) Appl. No.: 11/718,856

(22) PCT Filed: Nov. 7, 2005

(86) PCT No.: PCT/CH2005/000652

§ 371 (c)(1),
(2), (4) Date: Oct. 16, 2007

(87) PCT Pub. No.: WO2006/050628

PCT Pub. Date: May 18, 2006

(65) Prior Publication Data

US 2008/0200365 A1  Aug. 21, 2008

(30) Foreign Application Priority Data

Nov. 9, 2004  (GB) .................................. 0424643.5

(51) Int. Cl.
*C11D 3/50* (2006.01)
(52) U.S. Cl. ........................... 510/102; 510/106; 512/9; 568/375; 568/376
(58) Field of Classification Search ................ 510/102, 510/106; 512/9; 568/375, 376
See application file for complete search history.

(56) References Cited

U.S. PATENT DOCUMENTS 4,011,269 A  3/1977  Naf et al.

FOREIGN PATENT DOCUMENTS

WO  2004000776 A1  12/2003
WO  2006050628 A1  5/2006

OTHER PUBLICATIONS

K. Nawamaki et al., Phytochemistry 1996, vol. 43, issue 6, pp. 1175-1182 (abstract). No month available.*
Search Report from the Patent Office in Great Britain dated Feb. 17, 2005 for Application GB0424643.5.
Synthesis 2002, vol. 15, Kraft et al., pp. 2243-2253.
Written Opinion of the International Searching Authority for Application PCT/CH2005/000652.
Phtyochemistry, 1996, vol. 43(6) Nawamaki et al., pp. 1175-1182 & CAS Abstract Acc. No. 1996; 759630.
International Search Report dated Mar. 9, 2006 for Application PCT/CH2005/000652.
From Vetiver to Patchouli; Discovery of a New High-Impact Spirocyclic Patchouli Odorant, Kraft et al. No. 15, Jul. 14, 2005, pp. 3233-3245.

* cited by examiner

*Primary Examiner*—John R Hardee
(74) *Attorney, Agent, or Firm*—Norris McLaughlin & Marcus, PA

(57) ABSTRACT

Described are spirocyclic ketols of formula (I)

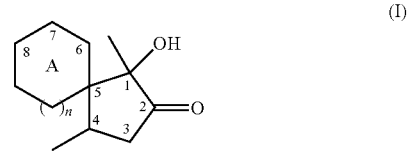

wherein n and A have the same meaning as given in the description. Also disclosed is a method for their production and flavour and fragrance compositions containing them.

9 Claims, 1 Drawing Sheet

SPIROCYCLIC KETOLS AND THEIR USE

This is an application filed under 35 USC 371 of PCT/CH2005/000652.

The present invention refers to novel compounds having patchouli-like odour notes. This invention relates furthermore to a method for their production and to flavour and fragrance compositions containing them.

Patchouli oil with its powerful woody-balsamic odor and well-balanced herbaceous, earthy, camphoraceous and floral facets today constitutes one of the most important natural perfumery raw materials in use. It is an essential building block especially for chypre and oriental fine fragrances, both feminine and masculine, and it is also of crucial importance in functional perfumery. Its most important olfactory constituent (−)-patchoulol, which makes up around 35-40 weight % of the essential oil, is structurally too complex to allow a synthetic approach that could compete with the price of the natural material. Thus, there is an ongoing demand in the fragrance and flavour industry for new compounds imparting, enhancing, or improving patchouli-like odour notes.

We have now found a novel class of spirocyclic ketols that possesses typical patchouli odours.

In a first aspect the present invention provides a compound of formula (I)

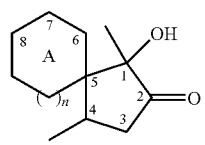

(I)

wherein n is 0, 1, 2, or 3; and ring A represents a cycloalkyl ring wherein up to 5 hydrogen atoms, i.e. none, 1, 2, 3, 4, or 5 are substituted by a methyl group; and the total number of carbon atoms of the compound of formula (I) is 11, 12, 13, 14, 15, or 16.

The compounds according to the present invention contain two or more stereocenters, and as such exist as mixtures of stereoisomers. They can be used as stereoisomeric mixtures, or may be resolved in diastereomerically and/or enantiomerically pure form. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methodology known in the art, e.g. preparative HPLC and GC or by stereoselective syntheses.

Particular preferred compounds of formula (I) are selected from the group consisting of (1R*,4S*,5S*,9R*)-1-hydroxy-1,4,7,7,9-pentamethylspiro[4.5]decan-2-one, (1R*,4R*,5S*,9R*)-1-hydroxy-1,4,7,7,9-pentamethylspiro[4.5]decan-2-one, (1R*,4R*)-1-hydroxy-1,4,7,7,9,9-hexamethylspiro[4.5]decan-2-one, (1R*,4S*,5r*,7R*,9S*)-1-hydroxy-1,4,7,9-tetramethylspiro[4.5]decan-2-one, (1R*,4R*,5r*,7R*,9S*)-1-hydroxy-1,4,7,9-tetramethylspiro[4.5]decan-2-one, and (1R*,4S*)-1-hydroxy-1,4-dimethylspiro[4.6]undecan-2-one.

It was found when the methyl groups at C-1 and C-4 are cis-configured with respect to one another, i.e. when C-1 and C-4 are unlike configured as (1R*,4S*), the compounds of the present invention have a lower odor threshold than the compounds wherein the methyl groups at C-1 and C-4 are trans-configured. The odor threshold of the unlike isomers is up to 270 times lower. Accordingly, compounds of formula (I) wherein the methyl groups at C-1 and C-4 are cis-configured with respect to one another are particularly preferred.

The compounds according to the present invention may be used alone or in combination with known odouriferous molecules selected from the extensive range of natural and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odourants in fragrance compositions, for example, carrier materials, and other auxiliary agents commonly used in the art.

Thus, in another aspect, the invention provides fragrance compositions comprising a compound of formula (I) or a mixture thereof.

The following list comprises examples of known odouriferous molecules, which may be combined with the compounds of the present invention:

ethereal oils and extracts, e.g. castoreum, costus root oil, oak moss absolute, geranium oil, jasmine absolute, patchouli oil, rose oil, sandalwood oil or ylang-ylang oil;

alcohols, e.g. citronellol, Ebanol®, eugenol, geraniol, Super Muguet, linalool, phenylethyl alcohol, Sandalore®, terpineol or Timberol®;

aldehydes and ketones, e.g. Azurone, α-amylcinnamaldehyde, Georgywood, hydroxycitronellal, Iso E Super, Isoraldeine, Hedione®, maltol, methyl cedryl ketone, methylionone or vanillin;

ether and acetals, e.g. Ambrox®, geranyl methyl ether, rose oxide or Spirambrene®;

esters and lactones, e.g. benzyl acetate, cedryl acetate, γ-decalactone, Helvetolide®, γ-undecalactone or vetivenyl acetate;

macrocycles, e.g. ambrettolide, ethylene brassylate or Exaltolide®;

heterocycles, e.g. isobutylchinoline.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odouriferous ingredients. The proportion is typically from 0.001 to 40 weight percent of the application. In one embodiment, compounds of the present invention may be employed in a fabric softener in an amount of from 0.001 to 0.05 weight percent. In another embodiment, compounds of the present invention may be used in an alcoholic solution in amounts of from 0.1 to 40 weight percent, more preferably between 0.1 and 5 weight percent. However, these values are given only by way of example, since the experienced perfumer may also achieve effects or may create novel accords with lower or higher concentrations.

The compounds of the present invention may be employed into the fragrance application simply by directly mixing them or a fragrance composition comprising them with the fragrance application, or they may, in an earlier step be entrapped with an entrapment material such as for example polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrant molecule upon application of an external stimulus such as light, enzyme, or the like, and then mixed with the application.

Thus, the invention additionally provides a method of manufacturing a fragrance application, comprising the incorporation as a fragrance ingredient of at least one compound of formula (I).

The compounds of the present invention may be prepared by epoxidation of the corresponding 4-methyl-1-methylenespiro[4.x]alkan-2-ones, which is available for example via the procedure as described by P. Kraft, R. Cadalbert, *Synthesis* 2002, 2243-2253, followed by reduction, e.g. with lithium aluminum hydride, and oxidation of the formed secondary alcohol function. Preferred oxidation agents are pyridinium chlorochromate (PCC), Dess-Martin periodinane and dimethyl sulfoxide (Swern oxidation). Further particulars as to reaction conditions are provided in the examples.

Figure 1:
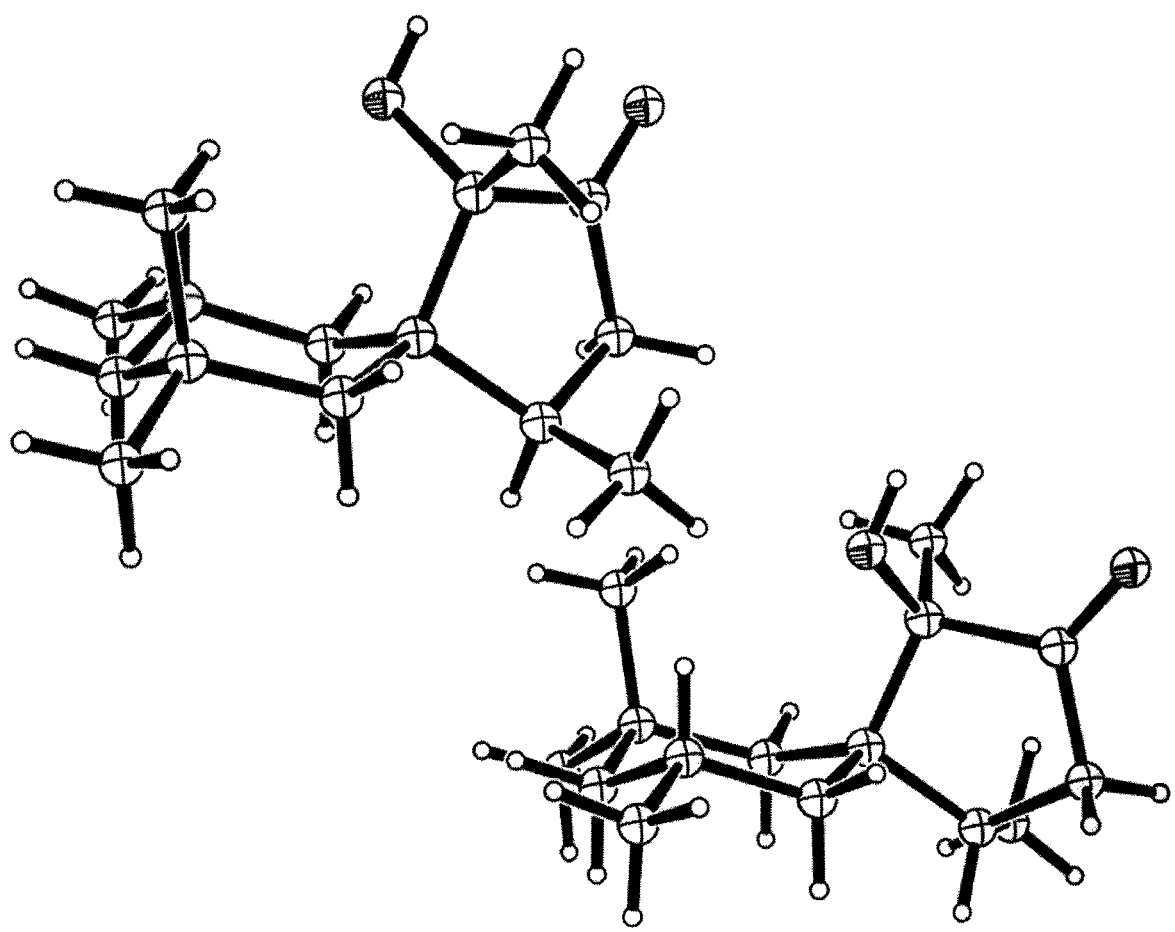
FIG. 1 shows the X-ray crystal structure of (1R*,4S*,5S*, 9R*)-1-hydroxy-1,4,7,7,9-pentamethylspiro[4.5]decan-2-one.

The invention is now further described with reference to the following non-limiting examples.

EXAMPLE 1

(1R*,4S*,5S*,9R*)-1-Hydroxy-1,4,7,7,9-pentamethylspiro[4.5]decan-2-one

At 0° C., a solution of 4,7,7,9-tetramethyl-1-methylenespiro[4.5]decan-2-one (1.43 g, 6.49 mmol), in $CH_2Cl_2$ (10 mL) was added dropwise within 45 min. to a stirred solution of 70% 3-chloroperbenzoic acid (1.76 g, 7.14 mmol) in $CH_2Cl_2$ (20 mL). After further stirring at 0° C. for 1 h, the cooling bath was removed, and the reaction mixture stirred for 3 d, with an additional portion of 70% 3-chloroperbenzoic acid (1.76 g, 7.14 mmol) being added after the first and second day. The insoluble material was removed by vacuum filtration and washed with $CH_2Cl_2$. The combined organic solutions were washed with 20% aq. $NaHSO_3$, halfconc. $NaHCO_3$, and water (50 mL), the aqueous washings again extracted with $CH_2Cl_2$ (50 mL). The combined organic extracts were dried ($Na_2SO_4$) and concentrated in a rotary evaporator. The resulting residue was purified by silica-gel FC (pentane/$Et_2O$, 19:1, $R_f$=0.11) to provide 6,6,8,10-tetramethyl-1-oxadispiro[2.0.5.3]dodecan-12-one (930 mg, 61%).

IR (ATR): ν=1753 (s, νC=O), 1457 (m, δH—C—H), 854 (m, δC—O—C, epoxide), 1196 (νC—O—C, epoxide) cm$^{-1}$. $^1$H NMR (CDCl$_3$): δ=0.68/0.72 (2t, J=12.5 Hz, 1H, 7-H$_{ax}$), 0.83/0.84 (2d, J=6.5 Hz, 3H, 8-Me), 0.94-1.04 (m, 1H, 9-H$_{ax}$), 0.91/0.93 (2s, 3H, 6-Me$_{eq}$), 0.95/0.96 (2s, 3H, 6-Me$_{ax}$), 1.02/1.10 (2d, J=6.5 Hz, 3H, 10-Me), 1.16-1.23 (m, 1H, 5-H$_{ax}$), 1.31-1.98 (m, 5H, 5-, 7-, 9-H$_{eq}$, 8-, 10-H), 1.99/ 2.07 (dd, J=18.5, 12.5 Hz, 1H, 11-H$_b$), 2.46/2.76 (dd, J=18.5, 7.0 Hz, 1H, 11-H$_a$), 2.63/2.74/2.93/2.96 (4d, J=6.5 Hz, 2H, 2-H$_2$). $^{13}$C NMR (CDCl$_3$): δ=13.7/17.2 (2q, 10-Me), 22.9/ 23.0 (2q, 8-Me$_{ax}$), 24.4/25.2 (2d, C-8), 26.0/26.1 (2q, 6-Me$_{eq}$), 31.1/34.9 (2s, C-6), 35.0/35.0 (2q, 6-Me$_{ax}$), 35.4/ 40.7 (2t, C-11), 36.7/40.9 (2d, C-10), 41.2/41.6 (2s, C-4), 41.8/42.3/42.5/44.6 (4t, C-5, -9), 48.2/48.7 (2t, C-2), 50.1/ 50.2 (2t, C-7), 67.1/70.0 (2s, C-3), 213.7/214.9 (2s, C-12). MS (70 eV): m/z (%)=236 (2) [M$^+$], 220 (28) [M$^+$-CH$_3$], 205 (73) [C$_{14}$H$_{21}$O$^+$], 178 (36) [M$^+$-CH$_3$—C$_2$H$_2$O], 163 (24) [M$^+$-C$_2$H$_2$O-2CH$_3$], 150 [C$_{11}$H$_{18}^+$], 135 (68) [C$_{11}$H$_{18}^+$—CH$_3$], 121 (59) [C$_{11}$H$_{18}^+$—C$_2$H$_5$], 107 (89) [C$_{11}$H$_{18}^+$—C$_3$H$_7$], 83 (80) [C$_6$H$_{11}^+$], 55 (88) [C$_4$H$_7^+$], 41 (100) [C$_3$H$_5^+$].

A solution of 6,6,8,10-tetramethyl-1-oxadispiro[2.0.5.3] dodecan-12-one (580 mg, 2.45 mmol) in $Et_2O$ (1.5 mL) was added dropwise with stirring at room temp. to a suspension of lithium aluminum hydride (280 mg, 7.36 mmol) in $Et_2O$ (3.0 mL). After stirring at ambient temp. for 30 min., the reaction was quenched by careful addition of water (5.0 mL) followed by aq. 5 N HCl (5.0 mL) at 0° C. The organic layer was separated, the aqueous one extracted with $Et_2O$ (2×25 mL). The combined organic extracts were washed with water (25 mL) and brine (25 mL), dried ($Na_2SO_4$) and concentrated on the rotary evaporator under reduced pressure to provide the crude corresponding diol (630 mg). A solution of pyridinium chlorochromate (1.06 g, 4.90 mmol) in $CH_2Cl_2$ (4.0 mL) was added at room temp. in one dash to a vigorously stirred suspension of Celite® (1.00 g) in $CH_2Cl_2$ (8.0 mL). Stirring was continued at this temp. for 10 min., prior to addition of the crude diol (630 mg) dissolved in $CH_2Cl_2$ (4.0 mL). After stirring for additional 30 min., the insoluble material was removed by vacuum filtration through a pad of Celite® with thorough washing with $CH_2Cl_2$. The organic extracts were concentrated under reduced pressure, and the resulting residue purified by silica-gel FC (pentane/$Et_2O$, 9:1, $R_f$=0.46) to afford as the most intensely smelling fraction (1R*,4S*,5S*, 9R*)-1-hydroxy-1,4,7,7,9-pentamethylspiro-[4.5]decan-2-one (30 mg, 5%) in form of colorless crystals, mp. 73-74° C.

IR (ATR): ν=1738 (s, νC=O), 1098 (s, νC—O), 3456 (s, νO—H), 1382 (m, δCH$_3$) cm$^{-1}$. $^1$H NMR(C$_6$D$_6$): δ=0.31 (dd, J=12.0, 12.0 Hz, 1H, 10-H$_{ax}$), 0.62 (dd, J=12.0, 12.0 Hz, 1H, 8-H$_{ax}$), 0.66 (d, J=7.5 Hz, 3H, 4-Me), 0.79 (dt, J=14.5, 2.5 Hz, 1H, 6-H$_{ax}$), 0.81 (d, J=6.5 Hz, 3H, 9-Me$_{eq}$), 0.95 (s, 3H, 7-Me$_{eq}$), 1.00 (s, 3H, 1-Me), 1.22 (s, 3H, 7-Me$_{ax}$), 1.35 (m$_c$, 1H, 4-H$_{ax}$), 1.36 (ddt, 1H, J=12.0, 6.0, 2.5, 8-H$_{eq}$), 1.50 (dt, J=14.5, 2.5 Hz, 1H, 6-H$_{eq}$), 1.57 (ddt, J=12.0, 6.0, 2.5 Hz, 1H, 10-H$_{eq}$), 1.62 (dd, J=20.0, 3.0 Hz, 1H, 3-H$_{eq}$), 2.27 (dd, J=20.0, 9.5 Hz, 1H, 3-H$_{ax}$), 2.34 (m$_c$, 1H, 9-H), 2.90 (s, 1H, O—H). $^1$H, $^1$H NOESY: 1-Me×4-Me, 1-Me×6-H$_{eq}$, 4-Me× 6-H$_{ax}$, 4-Me×6-H$_{eq}$, 7-Me$_{ax}$×9-H$_{ax}$. $^{13}$C NMR(C$_6$D$_6$): δ=18.4 (q, 4-Me), 23.6 (q, 9-Me), 24.1 (q, 1-Me), 26.4 (d, C-9), 26.5 (q, 7-Me$_{ax}$), 31.6 (s, C-7), 35.2 (q, 7-Me$_{eq}$), 39.6 (t, C-3), 40.6 (d, C-4), 42.0 (t, C-6), 46.0 (s, C-5), 47.8 (t, C-10), 49.2 (t, C-8), 81.3 (s, C-1), 221.2 (s, C-2). MS (70 eV): m/z (%)=238 (4) [M$^+$], 220 (1) [M$^+$-H$_2$O], 205 (1) [M$^+$-H$_2$O—CH$_3$], 168 (4) [C$_{11}$H$_{20}$O$^+$], 152 (39) [C$_{11}$H$_{20}^+$], 137 (11) [C$_{11}$H$_{20}^+$—CH$_3$], 123 (25)/109 (22)/95 (15) [C$_n$H$_{(2n-3)}^+$], 83 (100) [M$^+$-C$_9$H$_{15}$O$_2$], 69 (13) [C$_5$H$_9^+$], 55 (22) [C$_4$H$_7^+$], 43 (36) [C$_3$H$_7^+$].

Odor description: Strong, powerful, and characteristic of natural patchouli oil, with rich woody-ambery and tobacco-like facets

EXAMPLE 2

(1R*,4R*,5S*,9R*)-1-Hydroxy-1,4,7,7,9-pentamethylspiro[4.5]decan-2-one

Following the procedure detailed in Example 1, 1,4,7,7,9-pentamethylspiro-[4.5]decan-1,2-diol was prepared by reduction of 6,6,8,10-tetramethyl-1-oxadispiro-[2.0.5.3] dodecan-12-one with lithium aluminum hydride. A solution of Dess-Martin periodinane (780 mg, 1.84 mmol) in $CH_2Cl_2$ (20 mL) was added in one dash to a stirred solution of 1,4,7, 7,9-pentamethylspiro[4.5]decan-1,2-diol (400 mg, 1.66 mmol) in $CH_2Cl_2$ (15 mL). Stirring was continued at room temperature for 6 h, prior to quenching by dropwise addition of a solution of $Na_2S_2O_3$ (950 mg, 6.00 mmol) in satd. aq.

NaHCO$_3$ (40 mL). After stirring for 30 min., water (50 mL) was added, the organic layer was separated, and the aqueous one extracted with CH$_2$Cl$_2$ (50 mL). The combined organic extracts were washed with water (50 mL), dried (Na$_2$SO$_4$), vacuum-filtrated over a pad of Celite®, and concentrated on the rotary evaporator. The resulting residue (430 mg) was separated by repeated silica-gel FC (pentane/Et$_2$O, 9:1, R$_f$=0.48) to finally provide the weaker, less polar (1R*,4R*,5S*,9R*)-configured diastereoisomer of 1-hydroxy-1,4,7,7,9-pentamethylspiro[4.5]decan-2-one (60 mg, 15%) in pure form as colorless crystals, mp. 72-73° C.

IR (ATR): ν=1743 (s, νC═O), 1106/1081 (s, νC—O), 3470 (s, νO—H), 1385 (m, δCH$_3$) cm$^{-1}$. $^1$H NMR (CDCl$_3$): δ=0.64 (t, J=12.0 Hz, 1H, 8-H$_{ax}$), 0.72 (t, J=12.5 Hz, 1H, 10-H$_{ax}$), 0.78 (d, J=7.0 Hz, 3H, 9-Me), 0.94 (s, 3H, 7-Me$_{eq}$), 1.00 (d, J=6.5 Hz, 3H, 4-Me), 1.02 (d, J=12.5 Hz, 1H, 10-H$_{eq}$), 1.14 (s, 3H, 3H, 7-Me$_{ax}$), 1.17 (s, 3H, 1-Me), 1.20 (d, J=14.5 Hz, 1H, 6-H$_{ax}$), 1.35 (d, J=12.0 Hz, 1H, 8-H$_{eq}$), 1.45 (d, J=14.5 Hz, 1H, 6-H$_{eq}$), 1.82 (dd, J=16.5, 11.0 Hz, 1H, 3-H$_b$), 1.87 (m$_c$, 1H, 4H), 2.16 (m$_c$, 1 H, 9-H), 2.54 (dd, J=16.5, 6.5 Hz, 1H, 3-H$_a$), 2.84 (s, 1H, OH). $^1$H, $^1$H NOESY: 1-Me×4-H, 1-Me×7-Me$_{ax}$, 1-OH×7-Me$_{ax}$, 1-OH×9-H$_{ax}$, 7-Me$_{ax}$×9-H$_{ax}$. $^{13}$C NMR (CDCl$_3$): δ=14.5 (q, 4-Me), 21.4 (q, 1-Me), 23.3 (q, 9-Me), 25.3 (d, C-9), 26.3 (q, 7-Me$_{ax}$), 31.2 (s, C-7), 34.8 (q, 7-Me$_{eq}$), 34.8 (t, C-10), 35.8 (d, C-4), 38.5 (t, C-3), 40.9 (t, C-6), 47.0 (s, C-5), 49.0 (t, C-8), 83.9 (s, C-1), 221.6 (s, C-2) ppm. MS (70 eV): m/z (%)=238 (7) [M$^+$], 220 (1) [M$^+$-H$_2$O], 205 (1) [M$^+$-H$_2$O—CH$_3$], 168 (2) [C$_{11}$H$_{20}$O$^+$], 152 (40) [C$_{11}$H$_{20}$$^+$], 137 (12) [C$_{11}$H$_{20}$$^+$—CH$_3$], 123 (26)/109 (22)/95 (15) [C$_n$H$_{(2n-3)}$$^+$], 83 (100) [M$^+$-C$_9$H$_{15}$O$_2$], 67 (12) [C$_5$H$_7$$^+$], 55 (24) [C$_4$H$_7$$^+$], 43 (37) [C$_3$H$_7$$^+$].

Odor description: Nice, pleasant, and characteristic of natural patchouli oil, but about 270 times weaker than the (1R*,4S*,5S*,9R*)-isomer.

EXAMPLE 3

(1R*,4R*)-1-Hydroxy-1,4,7,7,9,9-hexamethylspiro [4.5]decan-2-one

A solution of 4,7,7,9,9-pentamethyl-1-methylenespiro [4.5]decan-2-one (19.0 g, 81.1 mmol), in CH$_2$Cl$_2$ (250 mL) was added dropwise at 0° C. during 2 h to a stirred solution of 70% 3-chloroperbenzoic acid (40.0 g, 162 mmol) in CH$_2$Cl$_2$ (500 mL). The cooling bath was removed after stirring for 2 h at 0° C., and stirring was continued for 5 d at room temp., with an additional portion of 70% 3-chloroperbenzoic acid (40.0 g, 162 mmol) being added after the second and forth day. The reaction mixture was then vacuum filtered over a pad of Celite®, and poured into ice-cold aq. 20% NaHSO$_3$ (1 L).

The formed precipitate was removed by vacuum filtration over Celite® and washed thoroughly with CH$_2$Cl$_2$. Water (200 mL) was added to the filtrate and pH 8 was adjusted by addition of satd. aq. Na$_2$CO$_3$ (ca. 200 mL). The organic layer was separated and washed with water (500 mL), the aqueous layer extracted with CH$_2$Cl$_2$ (500 mL). The combined organic extracts were dried (Na$_2$SO$_4$) and the solvent removed on the rotary evaporator. The resulting residue (18.8 g) was purified by silica-gel FC (pentane/Et$_2$O, 19:1, R$_f$=0.11) to provide (3R*,10S*)-6,6,8,8,10-pentamethyl-1-oxadispiro[2.0.5.3] dodecan-12-one (5.89 g, 29%).

IR (ATR): ν=1751 (s, νC═O), 1367 (s, δCH$_3$), 852 (m, δC—O—C, epoxide), 1458 (m, δH—C—H) cm$^{-1}$. $^1$H NMR (CDCl$_3$): δ=0.60 (d, J=15.0 Hz, 1H, 11-H$_{ax}$), 0.92/0.96 (2s, 6 H, 6-, 8-Me$_{ax}$), 1.00 (d, J=14.0 Hz, 1H, 5-H$_{ax}$), 1.08 (d, J=7.0 Hz, 3H, 10-Me), 1.10 (d, J=14.0 Hz, 1H, 7-H$_{ax}$), 1.14/1.17 (2s, 6H, 6-, 8-Me$_{eq}$), 1.34 (dt, J=14.0, 1.5 Hz, 1H, 7-H$_{eq}$), 1.59 (dt, J=15.0, 1.5 Hz, 1H, 11-H$_{eq}$), 1.69 (dt, J=14.0, 1.5 Hz, 1H, 5-H$_{eq}$), 2.11 (dd, J=18.5, 2.0, 1H, 9-H$_{ax}$), 2.70 (d, J=5.5 Hz, 1H, 2-H$_b$), 2.77 (dd, J=18.5, 7.0, 1H, 9-H$_{eq}$), 2.84 (quint. d, J=7.0, 2.0 Hz, 1H, 10-H), 3.00 (d, J=5.5 Hz, 1H, 2-H$_a$). $^{13}$C NMR (CDCl$_3$): δ=17.8 (q, 10-Me), 29.7 (2q, 6-, 8-Me$_{eq}$), 30.7/31.5 (2s, C-6, -8), 35.3 (d, C-10), 35.7 (2q, 6-, 8-Me$_{ax}$), 36.5 (t, C-11), 42.6 (s, C-4), 43.4/45.1 (2t, C-5, -9), 47.1 (t, C-2), 51.7 (t, C-7), 66.7 (s, C-3), 215.1 (s, C-12). MS (70 eV): m/z (%)=250 (2) [M$^+$], 234 (11) [M$^+$-O], 219 (100) [M$^+$-O—CH$_3$], 208 (6) [M$^+$-C$_3$H$_6$], 205 (7) [M$^+$-O—C$_2$H$_5$], 193 (29) [M$^+$-O—C$_3$H$_5$], 164 (22) [C$_{11}$H$_{16}$O+], 149 (52) [C$_{11}$H$_{16}$O+—CH$_3$], 121 (50) [C$_{11}$H$_{16}$O$^+$—C$_3$H$_7$], 91 (54) [C$_7$H$_7$$^+$], 79 (50) [C$_6$H$_7$$^+$], 55 (48) [C$_4$H$_7$$^+$], 41 (60) [C$_3$H$_5$$^+$].

Under N$_2$ atmosphere, a solution of (3R*,10S*)-6,6,8,8,10-pentamethyl-1-oxadispiro-[2.0.5.3]dodecan-12-one (5.65 g, 22.6 mmol) in Et$_2$O (10 mL) was added dropwise within 20 min. to a stirred suspension of lithium aluminum hydride (1.29 g, 33.8 mmol) in Et$_2$O (25 mL). The reaction mixture was refluxed for 3 h, and then stirred at room temp. over night, prior to quenching at 0° C. by addition of water (20 mL), followed by aq. HCl (5 N, 20 mL). The organic layer was separated, the aqueous one extracted with Et$_2$O (2×50 mL). The combined organic extracts were washed with water (50 mL) and brine (25 mL), dried (Na$_2$SO$_4$) and concentrated on the rotary evaporator. The resulting residue was purified by silica-gel FC (pentane/Et$_2$O, 4:1, R$_f$=0.10) to provide (1R*,2S*,4R*)-1,4,7,7,9,9-hexamethylspiro[4.5]decan-1,2-diol (4.82 g, 84%).

IR (ATR): ν=1098/1075 (s, νC—O), 1366 (m, δCH$_3$), 3411 (m, νO—H) cm$^{-1}$. $^1$H NMR (C$_6$D$_6$): δ=0.91/0.97 (s, 6H, 7-, 9-Me$_{ax}$), 0.93 (m$_c$, 2H, 6-H$_2$), 0.94 (s, 3H, 1-Me), 1.02 (d, 13.0 Hz, 1H, 8-H$_{ax}$), 1.03/1.07 (s, 6H, 7-, 9-Me$_{ax}$), 1.09 (d, J=15.0 Hz, 1H, 10-H$_{ax}$), 1.17 (d, J=13.0 Hz, 1H, 8-H$_{eq}$), 1.19 (ddd, J=14.0, 6.0, 4.5 Hz, 1H, 3-H$_b$), 1.24 (d, J=7.5 Hz, 3H, 4-Me), 1.44 (d, J=6.5 Hz, 1H, 2-OH), 1.78 (d, J=15.0 Hz, 1H, 10-H$_{eq}$), 1.81 (s, 1H, 1-OH), 2.11 (m$_c$, 1H, 4-H), 2.31 (dt, J=14.0, 9.0 Hz, 1H, 3-H$_a$), 3.59 (dt, J=9.0, 6.5 Hz, 1H, 2-H). $^1$H, $^1$H NOESY: 1-OH×10-H$_{ax}$, 1-OH×4-Me, 4-Me×10-H$_{eq}$, 1-Me×2-H, 2-H×6-H$_{eq}$, 1-OH×3-H$_b$, 3-H$_a$×6-H$_{eq}$, 6-H$_{eq}$×4-H. $^{13}$C NMR(C$_6$D$_6$): δ=21.4 (q, 4-Me), 21.7 (q, 1-Me), 30.2/30.6 (2q, 7-, 9-Me$_{ax}$), 36.3/43.5 (2t, C-6, -10), 36.6/37.0 (2q, 7-, 9-Me$_{eq}$), 38.3 (d, C-4), 40.7 (t, C-3), 49.7 (s, C-5), 51.8 (t, C-8), 77.0 (d, C-2), 84.0 (s, C-1) ppm. MS (70 eV): m/z (%)=254 (32) [M$^+$], 236 (2) [M$^+$-H$_2$O], 221 (8) [M$^+$-H$_2$O—CH$_3$], 203 (11) [M$^+$—2H$_2$O—CH$_3$], 191 (22) [C$_{14}$H$_{23}$$^+$], 166 (46) [C$_{12}$H$_{22}$$^+$], 151 (28) [C$_{12}$H$_{22}$$^+$—CH$_3$], 137 (54)/123 (39)/109 (61) [C$_n$H$_{(2n-3)}$$^+$], 97 (90) [C$_7$H$_{13}$$^+$], 87 (31) [C$_4$H$_7$O$_2$$^+$], 69 (63) [C$_5$H$_9$$^+$], 55 (68) [C$_4$H$_7$$^+$], 43 (100) [C$_3$H$_7$$^+$].

Under N$_2$ atmosphere with rigorous exclusion of moisture, a solution of dimethyl sulfoxide (340 mg, 4.40 mmol) in CH$_2$Cl$_2$ (1 mL) was injected via syringe at −70° C. within 5 min. into a stirred oxalyl chloride solution in CH$_2$Cl$_2$ (2 M, 1.10 ml, 2.20 mmol) diluted with CH$_2$Cl$_2$ (5 mL). After stirring at this temp. for 5 min., (1R*,2S*,4R*)-1,4,7,7,9,9-hexamethylspiro[4.5]decan-1,2-diol (510 mg, 2.00 mmol) dissolved in CH$_2$Cl$_2$ (1 mL) was injected during 5 min dropwise via syringe. Stirring was continued at −70° C. for 30 min., prior to injection of Et$_3$N (1.01 g, 10.0 mmol). The cooling bath was removed, and the reaction mixture allowed to warm to room temp., prior to pouring into water (50 mL). The organic layer was separated, the aqueous one extracted with CH$_2$Cl$_2$ (2×50 mL). The combined organic extracts were washed with water (50 mL), dried (Na$_2$SO$_4$), and concentrated on the rotary evaporator. Purification of the resulting residue by two silica-gel FC (pentane/Et$_2$O, 19:1, R$_f$=0.17)

furnished (1R*,4R*)-1-hydroxy-1,4,7,7,9,9-hexamethyl-spiro[4.5]decan-2-one (330 mg, 65%).

IR (ATR): ν=1741 (s, νC=O), 1362/1381 (m, δCH$_3$), 1066/1164/1128 (s, νC—O), 3468 (s, νO—H) cm$^{-1}$. $^1$H NMR (CDCl$_3$): δ=0.96-1.18 (m, 3H, 8-H$_{ax}$, 10-H$_2$), 0.91/0.99 (2s, 6H, 7-, 9-Me$_{eq}$), 1.02/1.11 (2s, 6H, 7-, 9-Me$_{ax}$), 1.07 (d, J=6.5 Hz, 3H, 4-Me), 1.21 (s, 3 H, 1-Me), 1.33 (d, J=13.0 Hz, 1H, 8-H$_{eq}$), 1.35 (d, J=14.5 Hz, 1H, 6-H$_{ax}$), 1.55 (d, J=14.5 Hz, 1H, 6-H$_{eq}$), 1.82 (dd, J=19.5, 10.0 Hz, 1H, 3-H$_b$), 2.04 (m$_c$, 1H, 4-H), 2.48 (dd, J=19.5, 9.0 Hz, 1H, 3-H$_a$), 2.86 (s, 1H, OH). $^{13}$C NMR (CDCl$_3$): δ=14.7 (q, 4-Me), 20.3 (q, 1-Me), 29.6/31.1 (2s, C-7, -9), 31.6/32.7/34.1/34.4 (4q, 7-, 9-Me$_2$), 33.6/37.5/38.8 (3t, C-3, -6, -10), 35.8 (d, C-4), 47.6 (s, C-5), 49.2 (t, C-8), 83.9 (s, C-1), 220.6 (s, C-2) ppm. MS (70 eV): m/z (%)=252 (7) [M$^+$], 237 (1) [M$^+$-CH$_3$], 219 (1) [M$^+$—CH$_3$—H$_2$O], 191 (3) [C$_{14}$H$_{23}$$^+$], 182 (4) [C$_{12}$H$_{22}$O$^+$], 166 (66) [C$_{12}$H$_{22}$$^+$], 151 (39) [C$_{12}$H$_{22}$$^+$—CH$_3$], 137 (40)/123 (23)/109 (37) [C$_n$H$_{(2n-3)}$$^+$], 97 (100) [C$_7$H$_{13}$$^+$], 55 (41) [C$_4$H$_7$$^+$], 43 (72) [C$_3$H$_7$$^+$]. C$_{16}$H$_{28}$O$_2$ (252.4): calcd. C, 76.14; H, 11.18; found C, 76.18; H, 11.13.

Odor description: Woody, patchouli.

EXAMPLE 4

A) (1R*,4S*,5r*,7R*,9S*)-1-Hydroxy-1,4,7,9-tetramethylspiro[4.5]decan-2-one

As described in Example 3, (4R*,5r*,7R*,9S*)-4,7,9-trimethyl-1-methylenespiro[4.5]-decan-2-one (5.21 g, 25.3 mmol), was reacted with 70% 3-chloroperbenzoic acid (2×8.72 g, 2×50.5 mmol) in CH$_2$Cl$_2$ (75 mL+150 mL) at room temp. for 4 d. Work-up with aq. 20% NaHSO$_3$ (200 mL) and purification by silica-gel FC (pentane/Et$_2$O, 9:1, R$_f$=0.22) provided 6,8,10-trimethyl-1-oxadispiro[2.0.5.3]dodecan-12-one (2.12 g, 38%).

IR (ATR): ν=1751 (s, νC=O), 1456 (s, δH—C—H), 865 (m, δC—O—C, epoxide), 1367 (m, δCH$_3$) cm$^{-1}$. $^1$H NMR (CDCl$_3$): δ=0.41/0.44 (2 pseudo q, J=12.5 Hz, 1H, 11-H$_{ax}$), 0.83/0.85/0.86/0.87 (4d, J=9.0, 6H, 6-, 8-Me), 0.90-2.13 (m, 8H, 6-, 8-, 9-H$_{ax}$, 5-, 7-H$_2$, 11-H$_{eq}$), 1.04/1.09 (2d, J=7.0 Hz, 3H, 10-Me), 2.70/2.74 (2dd, J=18.5, 9.0 Hz, 1H, 9-H$_{eq}$), 2.77-2.95 (m, 1H, 10-H), 2.82/2.82 (2d, J=6.5 Hz, 1H, 2-H$_b$), 2.96/2.97 (2d, J=6.5 Hz, 1H, 2-H$_a$). $^{13}$C NMR (CDCl$_3$): δ=13.8/16.9 (q, 10-Me), 22.8/22.9/22.9/23.0 (4q, 6-, 8-Me), 27.4/27.5/27.6/28.3 (4d, C-6, -8), 35.5/38.6/40.7/41.0/42.2/43.2 (6t, C-5, -9, -11), 43.5/43.7 (2t, C-7), 36.7/38.6 (d, C-10), 40.6/40.8 (2s, C-4), 48.6/49.1 (t, C-2), 66.9/69.7 (2s, C-3), 213.8/214.9 (2s, C-12). MS (70 eV): m/z (%)=222 (4) [M$^+$], 207 (7) [M$^+$-CH$_3$], 189 (33) [M$^+$-CH$_3$—H$_2$O$^+$], 165 (38) [C$_{11}$H$_{17}$O$^+$], 149 (23) [C$_{11}$H$_{17}$$^+$], 136 (39) [C$_{10}$H$_{16}$$^+$], 121 (38) [C$_9$H$_{13}$$^+$], 107 (71) [C$_8$H$_{11}$$^+$], 95 (71) [C$_7$H$_{11}$$^+$], 79 (70) [C$_6$H$_7$$^+$], 55 (80) [C$_4$H$_7$$^+$], 41 (100) [C$_3$H$_5$$^+$].

6,8,10-Trimethyl-1-oxadispiro[2.0.5.3]dodecan-12-one (2.11 g, 9.49 mmol) was reduced with lithium aluminum hydride (530 mg, 14.2 mmol) in refluxing Et$_2$O (5 mL+10 mL) for 90 min. Quenching with water (10 mL) and aq. HCl (5 N, 10 mL), usual extraction and purification by silica-gel FC (pentane/Et$_2$O, 2:1, R$_f$=0.20) furnished (4R*,5r*,7R*,9s*)-1,4,7,9-tetramethylspiro[4.5]decan-1,2-diol (1.88 g, 88%).

IR (ATR): ν=1455 (s, δH—C—H), 1074/1049 (s, νC—O), 1374 (m, δCH$_3$), 3397 (m, νO—H) cm$^{-1}$. $^1$H NMR(C$_6$D$_6$): δ=0.40/0.40/0.43 (3dd, J=12.0, 12.0 Hz, 1H, 10-H$_b$), 0.62-1.43 (m, 14H, 3-H$_b$, 6-, 8-H$_2$, 4-, 7-, 9-Me), 1.13/1.23/1.33 (3s, 3H, 1-Me), 1.62-2.23 (m, 6H, 2-OH, 4-, 7-, 9-H, 3-, 10-H$_a$), 2.74 (br. s, 1H, 1-OH), 3.95/3.97/3.60 (3dd, J=8.0, 6.0 Hz, 1H, 2-H). $^{13}$C NMR(C$_6$D$_6$): δ=14.5/15.2/15.8 (3q, 4-Me), 21.4/23.1/23.3 (3q, 1-Me), 23.4/23.4/23.5/23.6/25.3/25.4 (6q, 7-, 9-Me), 28.2/28.7/28.8/28.9/29.0/29.1 (6d, C-7, -9), 34.9/35.1/38.4/38.6/38.8/39.1 (6t, C-6, -10), 39.2/39.9/40.3 (3d, C-4), 41.3/43.5/43.9/44.1/44.4/65.8 (6t, C-3, -8), 46.7/47.5/49.0 (3s, C-5), 77.4/77.5/79.1 (3d, C-2), 81.3/81.8/84.0 (3s, C-1) ppm. MS (70 eV): m/z (%)=226 (13) [M$^+$], 208 (5) [M$^+$-H$_2$O], 193 (2) [M$^+$-H$_2$O—CH$_3$], 175 (3) [M$^+$—2H$_2$O—CH$_3$], 150 (10) [M$^+$—2H$_2$O-2CH$_3$], 138 (47) [C$_{10}$H$_{18}$$^+$], 109 (100) [C$_8$H$_{13}$$^+$], 95 (37) [C$_7$H$_{11}$$^+$], 81 (37) [C$_6$H$_9$$^+$], 55 (48) [C$_4$H$_7$$^+$], 43 (61) [C$_3$H$_7$$^+$].

Under N$_2$ atmosphere with rigorous exclusion of moisture, a solution of dimethyl sulfoxide (680 mg, 8.80 mmol) in CH$_2$Cl$_2$ (2 mL) was injected at −75° C. within 5 min. into a stirred oxalyl chloride solution in CH$_2$Cl$_2$ (2 M, 2.20 ml, 4.40 mmol) diluted with CH$_2$Cl$_2$ (10 mL). After stirring at this temp. for 5 min., (4R*,5r*,7R*,9S*)-1,4,7,9-tetramethylspiro[4.5]decan-1,2-diol (910 mg, 4.00 mmol) dissolved in CH$_2$Cl$_2$ (2 mL) was injected during 5 min dropwise via syringe. Stirring was continued at −70° C. for 15 min., prior to quenching with Et$_3$N (2.02 g, 20.0 mmol). The reaction mixture was allowed to warm to room temp., and poured into water (50 mL). The organic layer was separated, the aqueous one extracted with CH$_2$Cl$_2$ (2×50 mL). The combined organic extracts were washed with water (50 mL), and dried (Na$_2$SO$_4$). After removal of the solvent on a rotary evaporator, the resulting residue was purified by silica-gel FC (petane/Et$_2$O, 9:1, R$_f$=0.12) to provide (1R*,4S*,5r*,7R*,9S*)-1-hydroxy-1,4,7,9-tetramethylspiro[4.5]decan-2-one (530 mg, 59%).

IR (ATR): ν=1732 (s, νC=O), 3428 (s, νO—H), 1063/1089 (s, νC—O), 1359 (m, δCH$_3$) cm$^{-1}$. $^1$H NMR (CDCl$_3$): δ=0.46 (pseudo q, J=12.0 Hz, 1H, 8-H$_{ax}$), 0.74 (dq, J=13.5, 12.5 Hz, 1H, 6-H$_{ax}$), 0.83/0.88 (2d, J=6.5 Hz, 6H, 7-, 9-Me), 0.91 (dd, J=13.5, 13.5 Hz, 1H, 10-H$_{ax}$), 1.05 (d, J=7.5 Hz, 3H, 4-Me), 1.29 (s, 3H, 1-Me), 1.41 (dq, 13.5, 2.0 Hz, 1H, 10-H$_{eq}$), 1.67 (m$_c$, 1H, 9-H$_{ax}$), 1.69 (dq, 12.0, 2.0 Hz, 1H, 8-H$_{eq}$), 1.82 (dq, J=11.5, 2.0 Hz, 1H, 6-H$_{eq}$), 1.91 (me, 1H, 7-H$_{ax}$), 1.96 (dd, J=19.0, 8.0 Hz, 1H, 3-H$_b$), 2.09 (ddq, J=7.5, 7.5, 7.5 Hz, 1H, 4-H), 2.26 (s, 1H, O—H), 2.57 (dd, J=19.0, 9.0 Hz, 1H, 3-H$_a$). $^1$H, $^1$H NOESY: 1-Me×4-Me, 1-Me×10-H$_{ax}$, 1-Me×10-H$_{eq}$, 1-Me×9-H$_{ax}$, 4-H×6-H$_{ax}$. $^{13}$C NMR (CDCl$_3$): δ=15.8 (q, 4-Me), 22.7 (q, 1-Me), 23.2/23.3 (2q, 7-, 9-Me), 28.4 (d, C-9), 29.0 (d, C-7), 35.8 (t, C-10), 37.4 (d, C-4), 40.5 (t, C-3), 41.1 (t, C-6), 43.8 (t, C-8), 46.7 (s, C-5), 81.2 (s, C-1), 219.6 (s, C-2). MS (70 eV): m/z (%)=224 (14) [M$^+$], 206 (3) [M$^+$-H$_2$O], 191 (2) [M$^+$-H$_2$O—CH$_3$], 154 (12) [C$_{10}$H$_{18}$O$^+$], 138 (60) [C$_{10}$H$_{18}$$^+$], 123 (19)/109 (100)/95 (27) [C$_n$H$_{(2n-3)}$$^+$], 81 (29) [C$_6$H$_9$$^+$], 69 (21) [C$_5$H$_9$$^+$], 55 (29) [C$_4$H$_7$$^+$], 43 (51) [C$_3$H$_7$$^+$].

Odor description: Typical patchouli odor.

B) (1R*,4R*,5r*,7R*,9S*)-1-Hydroxy-1,4,7,9-tetramethylspiro[4.5]decan-2-one

Besides (1R*,4S*,5r*,7R*,9S*)-1-hydroxy-1,4,7,9-tetramethylspiro[4.5]decan-2-one, the silica-gel FC (petane/Et$_2$O, 9:1, R$_f$=0.27) of Example 4A also furnished (1R*,4R*,5r*,7R*,9S*)-1-hydroxy-1,4,7,9-tetramethylspiro[4.5]decan-2-one (220 mg, 25%).

IR (ATR): ν=1744 (s, νC=O), 1095/1119 (m, νC—O), 1371 (m, δCH$_3$), 3487 (m, νO—H) cm$^{-1}$. $^1$H NMR (CDCl$_3$): δ=0.41 (pseudo q, J=12.0 Hz, 1H, 8-H$_{ax}$), 0.79/0.88 (2d, J=6.5 Hz, 6H, 7-, 9-Me), 0.81 (dd, J=13.5, 13.5 Hz, 1H, 6-H$_{ax}$), 0.98 (dd, J=13.5, 13.5 Hz, 1H, 10-H$_{ax}$), 1.01 (d, J=7.0 Hz, 3H, 4-Me), 1.08 (dq, J=15.5, 2.0 Hz, 1H, 6-H$_{eq}$), 1.17 (s, 3H, 1-Me), 1.55 (dq, 13.5, 2.0 Hz, 1H, 10-H$_{eq}$), 1.68 (dq, 12.0, 2.0 Hz, 1H, 8-H$_{eq}$), 1.77 (m, 1H, 9-H$_{ax}$), 1.85 (dd, J=19.0, 11.0 Hz, 1H, 3-H$_b$), 1.93 (m$_c$, 1H, 4-H), 2.23 (m$_c$, 1H, 7-H$_{ax}$), 2.53 (dd, J=19.0, 8.5 Hz, 1H, 3-H$_a$), 2.76 (s, 1H, 10-H). $^1$H, $^1$H NOESY: 4-Me×3-H, 1-Me×4-Me, 1-Me×6-H$_{eq}$, 4-Me×10-H$_{ax}$. $^{13}$C NMR (CDCl$_3$): δ=14.3 (q, 4-Me), 21.3 (q, 1-Me), 22.9/23.4 (2q, 7-, 9-Me), 28.0 (d, C-9), 28.5 (d, C-7), 34.8 (t, C-6), 35.3 (d, C-4), 38.7 (t, C-10), 38.9 (t, C-3), 44.1 (t, C-8), 47.1 (s, C-5), 84.5 (s, C-1), 221.1 (s, C-2). MS (70 eV): m/z (%)=224 (15) [M$^+$], 206 (2) [M$^+$-H$_2$O], 191 (1) [M$^+$-H$_2$O—CH$_3$], 154 (10) [C$_{10}$H$_{18}$O$^+$], 138 (60) [C$_{10}$H$_{18}$$^+$], 123 (19)/109 (100)/95 (26) [C$_n$H$_{(2n-3)}$$^+$], 81 (29) [C$_6$H$_9$$^+$], 67 (22) [C$_5$H$_7$$^+$], 55 (28) [C$_4$H$_7$$^+$], 43 (53) [C$_3$H$_7$$^+$].

Odor description: Patchouli-like, woody odor.

EXAMPLE 5

(1R*,4S*)-1-Hydroxy-1,4-dimethylspiro[4.6]undecan-2-one

Following the same general procedure of Example 3, 4-methyl-1-methylenespiro[4.6]undecan-2-one (5.29 g, 27.5 mmol) was reacted with 70% 3-chloroperbenzoic acid (13.6 g, 55.0 mmol) in CH$_2$Cl$_2$ (75 mL+150 mL) at room temp. for 4 d, with additional portions of 70% 3-chloroperbenzoic acid (7.00 g, 28.4 mmol) being added after every day. Work-up with aq. 20% NaHSO$_3$ (250 mL) and purification by silica-gel FC (pentane/Et$_2$O, 9:1, R$_f$=0.19) provided (3R*,11S*)-11-methyl-1-oxadispiro[2.0.6.3]tridecan-13-one (1.01 g, 18%), besides the (3R*,11R*)-diastereomer (R$_f$=0.14, 820 mg, 14%).

IR (ATR): ν=1749 (s, νC=O), 1460 (s, δH—C—H), 830 (m, δC—O—C, epoxide), 1381 (m, δCH$_3$) cm$^{-1}$. $^1$H NMR (CDCl$_3$): δ=1.05 (d, J=7.0 Hz, 3H, 11-Me), 1.35-1.66 (m, 12H, 5-H$_2$-10-H$_2$), 1.99 (dd, J=19.0, 3.0 Hz, 1H, 12-H$_b$), 2.37 (dqd, J=7.5, 7.0, 3.0 Hz, 1H, 11-H), 2.63 (dd, J=19.0, 7.5 Hz, 1H, 12-H$_a$), 2.93 (d, J=6.5 Hz, 1H, 2-H$_b$), 2.98 (d, J=6.5 Hz, 1H, 2-H$_a$). $^{13}$C NMR (CDCl$_3$): δ=17.5 (q, 11-Me), 22.7/23.0 (2t, C-6, -9), 30.1/30.6/31.2/35.8 (4t, C-5, -7, -8, -10), 35.5 (d, C-11), 43.1 (s, C-4), 51.6 (t, C-2), 67.5 (s, C-3), 215.3 (s, C-13). MS (70 eV): m/z (%)=208 (2) [M$^+$], 192 (10) [C$_{13}$H$_{20}$O$^+$], 177 (9) [C$_{13}$H$_{20}$O$^+$—CH$_3$], 164 (17) [C$_{13}$H$_{20}$O$^+$—CO], 150 (24) [C$_{11}$H$_{18}$$^+$], 135 (17) [C$_{11}$H$_{18}$$^+$—CH$_3$], 122 (51) [C$_{11}$H$_{18}$$^+$—C$_2$H$_4$], 107 (46) [C$_8$H$_{11}$$^+$], 93 (65) [C$_7$H$_9$$^+$], 79 (100) [C$_6$H$_7$$^+$], 67 (41) [C$_5$H$_7$$^+$], 41 (50) [C$_3$H$_5$$^+$].

(3R*,11S*)-11-Methyl-1-oxadispiro[2.0.6.3]tridecan-13-one (800 mg, 3.84 mmol) was reduced with lithium aluminum hydride (440 mg, 11.5 mmol) in Et$_2$O (2 mL+4 mL) at ambient temp. for 16 h. Quenching with water (5 mL) and aq. HCl (5 N, 5 mL), usual extraction and purification by silica-gel FC (pentane/Et$_2$O, 2:1, R$_f$=0.16) furnished (1R*,2R*,4S*)-/(1R*,2S*,4S*)-1,4-dimethylspiro[4.6]undecane-1,2-diol (620 mg, 76%).

IR (ATR): ν=1076/1049 (s, νC—O), 1455/1474/1444 (s, δH—C—H), 1377 (m, δCH$_3$), 3388 (m, νO—H) cm$^{-1}$. $^1$H NMR(C$_6$D$_6$): δ=0.84/0.91 (2d, J=7.0 Hz, 3H, 4-Me), 1.06/1.09 (2s, 3H, 1-Me), 1.07-2.15 (m, 16H, 1-, 2-OH, 3-H$_2$, 6-H$_2$-11-H$_2$), 1.94/2.29 (2m$_c$, 1H, 4-H), 3.58 (dt, J=10.0, 5.0 Hz)/3.60 (t, J=7.0 Hz, 1H, 2-H). $^{13}$C NMR (C$_6$D$_6$): δ=15.7/16.3 (2q, 4-Me), 20.1/21.2 (2q, 1-Me), 24.8/25.0/25.1 125.2 (4t, C-7, -10), 29.1/30.0 132.5/32.8/32.9/33.0/33.2/35.7 (8t, C-6, -8, -9, -11), 39.5/40.5 (2t, C-3), 41.0/41.3 (2d, C-4), 50.0/51.4 (2s, C-5), 75.9/79.8 (2d, C-2), 82.9/84.9 (2s, C-1) ppm. MS (70 eV): m/z (%)=212 (12) [M$^+$], 194 (4) [M$^+$-H$_2$O], 192 (2) [M$^+$-H$_2$O—H$_2$], 179 (4) [M$^+$-H$_2$O—CH$_3$], 167 (5) [M$^+$-C$_2$H$_5$O], 149 (22) [C$_{11}$H$_{17}$$^+$], 136 (17) [C$_{10}$H$_{16}$$^+$], 124 (92) [C$_9$H$_{16}$$^+$], 109 (20) [C$_9$H$_{16}$$^+$—CH$_3$], 107 (28) [C$_{10}$H$_{16}$$^+$—C$_2$H$_5$], 95 (100) [C$_7$H$_{11}$$^+$], 87 (36) [C$_4$H$_7$O$_2$$^+$], 81 (96) [C$_6$H$_9$$^+$], 74 (49) [C$_3$H$_6$O$_2$$^+$], 67 (79) [C$_5$H$_7$$^+$], 55 (92) [C$_4$H$_7$$^+$], 43 (100) [C$_3$H$_7$$^+$].

As described in Example 1, (1R*,2R*,4S*)-/(1R*,2S*,4S*)-1,4-dimethylspiro[4.6]-undecane-1,2-diol (570 mg, 2.69 mmol) was oxidized with pyridinium chlorochromate (630 mg, 2.95 mmol) on Celite® (630 mg) in CH$_2$Cl$_2$ (10+12 mL) at room temp. for 12 h. Standard work-up by vacuum filtration over a pad of Celite® furnished after purification by silica-gel FC (pentane/Et$_2$O, 9:1, R$_f$=0.10) (1R*,4S*)-1-hydroxy-1,4-dimethylspiro[4.6]undecan-2-one (21 mg, 4%).

IR (ATR): ν=1733 (s, νC=O), 1100/1059 (s, νC-0), 3429 (s, νO—H), 1382 (m, δCH$_3$) cm$^{-1}$. $^1$H NMR (CDCl$_3$): δ=1.14 (d, J=7.0 Hz, 3H, 4-Me), 1.24 (s, 3H, 1-Me), 1.26-1.65 (m, 12H, 6-H$_2$-11-H$_2$), 1.93 (dd, J=19.5, 8.0 Hz, 1H, 3-H$_b$), 2.08 (s, 1H, O—H), 2.32 (ddq, J=9.5, 8.0, 7.0 Hz, 1H, 4-H), 2.54 (dd, J=19.5, 9.5 Hz, 1H, 3-H$_a$). $^1$H, $^1$H NOESY: 1-Me×4-Me, 3-H$_b$×4-Me, 1-Me×3-H$_b$. $^{13}$C NMR (CDCl$_3$): δ=16.9 (q, 4-Me), 20.5 (q, 1-Me), 23.9/24.3 (2t, C-7, -10), 29.0/31.8/31.9/35.2 (4t, C-6, -8, -9, 11), 37.0 (d, C-4), 40.7 (t, C-3), 48.6 (s, C-5), 82.3 (s, C-1), 219.1 (s, C-2). MS (70 eV): m/z (%)=210 (16) [M$^+$], 192 (3) [M$^+$-H$_2$O], 177 (3) [M$^+$-H$_2$O—CH$_3$], 124 (99) [C$_9$H$_{16}$$^+$], 109 (13) [C$_8$H$_{13}$$^+$], 95 (100) [C$_7$H$_{11}$$^+$], 81 (66) [C$_6$H$_9$$^+$], 67 (55) [C$_5$H$_7$$^+$], 55 (45) [C$_4$H$_7$$^+$], 43 (77) [C$_3$H$_7$$^+$].

Odor description: woody, herbaceous, camphor.

EXAMPLE 6

The following compound may also be prepared according to the general procedure as described in Example 1: (1R*,4S*,5S*)-1-hydroxy-1,4,7,7-tetramethylspiro[4.5]decan-2-one and (1R*,4R*,5S*)-1-hydroxy-1,4,7,7-tetramethylspiro[4.5]decan-2-one.

EXAMPLE 7

X-Ray Crystal Structure of (1R*,4S*,5S*,9R*)-1-Hydroxy-1,4,7,7,9-pentamethylspiro[4.5]decan-2-one (FIG. 1)

Crystal data and structure refinement: Empirical formula C$_{15}$H$_{26}$O$_2$, molecular mass 238.36, crystal dimensions 0.5×0.4×0.01 mm, temperature 150 K, wavelength 0.71073 Å, triclinic crystal system, space group P-1, unit cell dimensions a=9.6129(19) Å, b=13.368(3) Å, c=13.402(3) Å, α=112.17(3)°, β=104.57(3)°, γ=103.52(3)°, V=1436.1(5) Å$^3$, Z=4, ρ=1.102 mg m$^{-3}$, μ(Mo$_{Kα}$)=0.071 mm$^{-1}$, F(000) 528, θ range 2.35-26.00°, limiting indices −11≦h≦11, −16≦k≦16, −15≦/≦16, total reflections collected 10964, symmetry-independent reflections 5162, R$_{int}$=0.0283, refinement full-matrix least squares on F$^2$, data 5162, parameters 319, goodness-of-fit on F$^2$ 0.877, final R indices [I>2σ(I)], R$_1$=0.0392, wR$_2$=0.0861, R indices (all data) R$_1$=0.0711, wR$_2$=0.0945, Δρ (max, min)=0.265, −0.124 e Å$^{-3}$. C$_{15}$H$_{26}$O$_2$ (238.4): calcd. C, 75.58; H, 10.99; found C, 75.56; H, 10.99.

EXAMPLE 8

Fruity-Floral Chypre Feminine Fine Fragrance

| Ingredient | Parts per weight |
| --- | --- |
| 1. Benzyl acetate | 150 |
| 2. Bergamot oil (Italy) | 550 |
| 3. 4-tert-Butyl-α-methyldihydrocinnamaldehyde | 1000 |
| 4. Coumarin | 50 |
| 5. α-Damascone | 5 |
| 6. Ethyl linalool | 1000 |
| 7. Geraniol | 250 |
| 8. Geranyl acetate | 80 |
| 9. (3Z)-Hex-3-en-1-ol | 10 |
| 10. (3Z)-Hex-3-en-1-yl salicylate | 400 |
| 11. β-Ionone | 200 |
| 12. 2-Isobutyl-4-methyltetrahydro-2H-pyran-4-ol | 300 |
| 13. Iso E Super (2,3,8,8-tetramethyl-1,2,3,4,5,6,7,8-octahydro-2-naphthalenyl methyl ketone and isomers) | 300 |
| 14. Methyl dihydrojasmonate | 3400 |
| 15. 2-Phenylethanol | 200 |
| 16. 1-Phenylethyl acetate | 50 |
| 17. 1,13-Tridecanedioic acid ethylene ester | 1000 |
| 18. γ-Undecalactone | 5 |
| 19. Vanillin | 50 |
| 20. (1R*, 4S*, 5S*, 9R*)-1-Hydroxy-1,4,7,7,9-pentamethyl-spiro[4.5]decan-2-one @ 10% in dipropylene glycol | 1000 |
| Total: | 10,000 |

(1R*,4S*,5S*,9R*)-1-Hydroxy-1,4,7,7,9-pentamethyl-spiro[4.5]decan-2-one confers to this modern floral-fruity feminine fine fragrance body, warmth and depth, and a typical patchouli character that blends well with the rosy elements of this composition and gives the fragrance a twist in the chypre direction. In comparison with the same amount of patchouli oil, the new material has a stronger olfactory impact on the overall composition, and makes the top note less camphoraceous, while providing the same warmth, sensuality, and balsamic effect at less dosage.

EXAMPLE 9

Leathery-Woody Masculine Perfume

| Ingredient | Parts per weight |
| --- | --- |
| 1. Baies Roses $CO_2$ extract | 20 |
| 2. Benzyl salicylate | 1000 |
| 3. Bergamot oil (Italy) | 100 |
| 4. Carrot seed oil | 10 |
| 5. Cedarwood oil (Atlas) | 20 |
| 6. Cedryl methyl ether | 100 |
| 7. Cinnamyl cinnamate | 50 |
| 8. 6,7-Dihydro-1,1,2,3,3-pentamethyl-4(5H)-indanone | 20 |
| 9. 2-Ethyl-4-(2,2,3-trimethyl-3-cyclopenten-1-yl)-2-buten-1-ol | 50 |
| 10. 4-Formyl-2-methoxyphenyl isobutyrate @ 10% in dipropylene glycol | 20 |
| 11. 16-Hexadec-9-enolide | 50 |
| 12. 3-trans-Isocamphylcyclohexanol | 250 |
| 13. Kephalis (4-(1-ethoxyvinyl)-3,3,5,5-tetramethyl-cyclohexanone and isomers) | 1500 |

-continued

| Ingredient | Parts per weight |
| --- | --- |
| 14. Linalool | 150 |
| 15. Methyl dihydrojasmonate | 500 |
| 16. 3,4-Methylenedioxybenzaldehyde @ 1% in dipropylene glycol (DPG) | 50 |
| 17. Methyl 2,4-dihydroxy-3,6-dimethylbenzoate | 50 |
| 18. 6-(1-Methylpropyl)quinoline @ 10% in DPG | 50 |
| 19. 3a,6,6,9a-Tetramethyldodecahydronaphtho[2,1-b]furan | 10 |
| 20. 1,13-Tridecanedioic acid ethylene ester | 1000 |
| 21. (1R*, 4S*, 5S*, 9R*)-1-Hydroxy-1,4,7,7,9-pentamethyl-spiro[4.5]decan-2-one @ 10% in dipropylene glycol | 5000 |
| Total: | 10,000 |

(1R*,4S*,5S*,9R*)-1-Hydroxy-1,4,7,7,9-pentamethyl-spiro[4.5]decan-2-one confers to this woody-ambery, leathery masculine perfume personality and a sophisticated but natural and characteristic touch of patchouli oil. It harmoniously blends in with the main woody theme and forms the heart note of this typical note, without having any unpleasant camphoraceous or dirty impact on the transparent hesperidic-spicy top note. In comparison with the same amount of patchouli oil, the new material is stronger, more present and pleasant, and free from a herbal, dirty and camphoraceous aspects in the top note.

The invention claimed is:

1. A compound of formula (I)

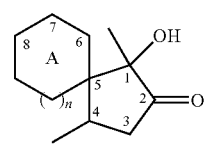

(I)

wherein n is 0, 1, 2, or 3; and ring A represents a cycloalkyl ring wherein up to 5 hydrogen atoms are substituted by a methyl group; and the total number of carbon atoms of the compound of formula (I) is 11, 12, 13, 14, 15, or 16.

2. A compound according to claim 1 wherein the methyl groups at C1 and C4 are cis-configured with respect to one another.

3. A method of manufacturing a fragrance application, comprising the incorporation of an effective amount of a compound of formula (I) as defined in claim 2.

4. A compound according to claim 1 selected from the group consisting of (1R*,4S*,5S*,9R*)-1-hydroxy-1,4,7,7,9-pentamethylspiro[4.5]decan-2-one, (1R*,4R*,5S*,9R*)-1-hydroxy-1,4,7,7,9-pentamethylspiro[4.5]decan-2-one, (1R*,4R*)-1-hydroxy-1,4,7,7,9,9-hexamethylspiro[4.5]decan-2-one, (1R*,4S*,5r*,7R*,9S*)-1-hydroxy-1,4,7,9-tetramethylspiro[4.5]decan-2-one, (1R*,4R*,5r*,7R*,9S*)-1-hydroxy-1,4,7,9-tetramethylspiro[4.5]decan-2-one, and (1R*,4S*)-1-hydroxy-1,4-dimethylspiro[4.6]undecan-2-one.

5. A fragrance composition comprising a compound according to claim 1.

6. A fragrance application comprising a compound claim 1.

7. A fragrance application according to claim 6 wherein the fragrance application is selected from: perfume, household product, laundry product, body care product, cosmetic product and air-care product.

8. A method of manufacturing a fragrance application, comprising the incorporation of an effective amount of a compound of formula (I) as defined in claim 1.

9. A method according to claim 8 wherein the fragrance application is selected from: perfume, household product, laundry product, body care product, cosmetic product and air-care product.

\* \* \* \* \*